Figure 1:
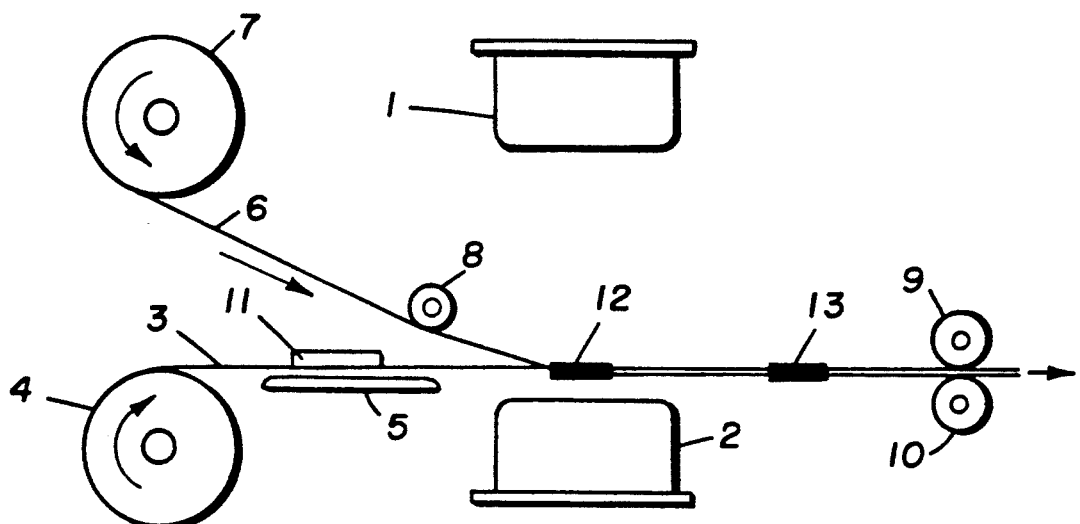

United States Patent

Mathews et al.

Patent Number: 5,309,768
Date of Patent: May 10, 1994

[54] AUTOMATION OF TEST INSTRUMENTS

[75] Inventors: Michael Mathews; David G. Rusling; Michael J. Stolc, all of Wiltshire, England; Robert I. Barker, Akron, Ohio

[73] Assignee: Monsanto Company, St. Louis, Mo.

[21] Appl. No.: 872,205

[22] Filed: Apr. 23, 1992

[30] Foreign Application Priority Data

Apr. 26, 1991 [GB] United Kingdom ............... 9108960
Oct. 29, 1991 [GB] United Kingdom ............... 9122869

[51] Int. Cl.$^5$ ............................................. G01N 3/24
[52] U.S. Cl. ..................................................... 73/846
[58] Field of Search .......................... 73/847, 843, 846

[56] References Cited

U.S. PATENT DOCUMENTS

| | | | |
|---|---|---|---|
| 3,650,698 | 3/1972 | Adler | 23/253 R |
| 4,395,125 | 7/1983 | Kaneko et al. | 356/400 |
| 4,552,025 | 11/1985 | Barker et al. | 73/846 |
| 4,584,882 | 4/1986 | Tosaki | 73/847 |
| 4,953,406 | 9/1990 | Putman | 73/843 |

FOREIGN PATENT DOCUMENTS 2214127  8/1974  France .

OTHER PUBLICATIONS

Derwent Abstract, Soviet Inventions Illustrated Sep. 22, 1982–Voron Tech. Inst.
American Society for Testing and Materials (1990) (ASTM) D1646-89 vol. 9, pp. 307–314 (310).

Primary Examiner—Jerry W. Myracle
Attorney, Agent, or Firm—Gordon B. Seward

[57] ABSTRACT

A method of operating an instrument for testing the physical properties of materials in which each of a series of samples of the material to be tested is placed in a test position located between dies, the dies are closed to mould the material to a test shape, a test is carried out on the sample in the mould and after completion of the test the dies are opened and the sample is removed from the test position is characterised in that a film of material which is substantially non-adhesive to the dies under the conditions of the test is provided to cover those surfaces of the sample which, in the absence of the film, would be in contact with the dies, each sample in turn is conveyed to the test position, and mechanical elements are provided for removing each sample from the test position after the completion of the test. Apparatus suitable for use in the method of the invention is also provided.

14 Claims, 1 Drawing Sheet

AUTOMATION OF TEST INSTRUMENTS

This invention relates to the automation of instruments for the testing of physical properties of materials, in which during the test a sample of material is held in a test position between two dies.

More particularly, the invention is concerned with the automation of instruments for determining the viscoelastic properties of rubber and similar materials, in which a sample of material is located in a cavity between two relatively rotatable dies, an oscillatory torque is applied to one die, the torque induced in the other die is measured, and information concerning the properties of the material is derived from such measurements. Examples of such instruments are described in U.S. Pat. No. 4,552,025 and U.S. Pat. No. 4,584,882.

Efforts to automate the operation of such instruments have hitherto been directed to the use of mechanical devices which strip the sample from the mould after the completion of the test in a manner analogous to hand operation. The fact that some samples do not strip cleanly from the mould (this applies particularly to certain rubbers which are designed to bond to metallic surfaces during vulcanisation) militates against success when attempting to automate the operation of such instruments. The use of heat-resistant film as a barrier between a sample to be tested and the dies of the Mooney viscometer (which is a different kind of instrument) is recommended for use where the sample is a 'sticky' compound, in ASTM D1646.

The present invention provides a method of operating an instrument for testing the physical properties of materials in which each of a series of samples of the material to be tested is placed in a test position located between dies, the dies are closed to mould the material to a test shape, a test is carried out on the sample in the mould, and after the completion of the test the dies are opened and the sample is removed from the test position, characterised in that a film of material which is substantially non-adhesive to the dies under the conditions of the test is provided to cover those surfaces of the sample which, in the absence of the film, would be in contact with the dies during the test, each sample in turn is conveyed to the test position, and mechanical means are provided for removing each sample from the test position after the completion of the test. In some embodiments of the invention, it is convenient to have an arrangement in which film which extends beyond the surface of the sample is utilised in effecting at least the removal of the samples.

In a preferred method of operation, the mechanical means at least for the removal of the samples comprise a strip of film which passes through the test position and is arranged to act as a conveyer belt. Samples to be tested are loaded onto the strip upstream of or at the test position such that the strip forms a barrier between the sample and the surface of one die when the sample is in the test position, and, before closure of the dies is complete, film is interposed between the sample and the surface of the second die. When the test is complete, the film-enclosed sample is removed from the test position by activation of conveyor belt drive means.

Loading of samples onto the strip will normally be done by automatic mechanical loading means, for example, a pivotal or retractable arm having gripping means or a vacuum head which transfers the samples from a position external to the conveyor strip on to the strip. Manual loading of the samples is possible, however.

If each sample is loaded onto the strip at a position upstream of the test position, then the strip, in its function as a conveyor belt, is part of the mechanism for conveying each sample in turn to the test position.

A preferred procedure is to employ two separate strips of film which are unwound by intermittent activation of conveyor belt drive means from rolls upstream of the test position and which, when the sample is in the test position, provide barriers between the sample and the surfaces of the dies with which the sample would otherwise be in contact.

Alternatively, it is possible to use a single strip of film having a longitudinal fold. The arrangement is such that at the appropriate stage, folding of the strip is incomplete and the free edges of the strip are sufficiently separated to allow lateral insertion of samples. At a later stage provision is made for ensuring that folding is completed so that the edge regions of the film on the opposite side of the sample from the fold lie firmly against each other on entry of the sample into the test position or on closure of the dies.

In an alternative embodiment of the invention, each sample is encased in an individual sachet of film, and the sachets are placed in a position external to the test position of the instrument, for example a cassette or rack in such a way that a portion of each sachet is accessible to transfer means. Such transfer means can comprise gripping or vacuum means located at the end of a moveable arm, arranged so that each sample is taken in turn from the cassette or rack and placed in the test position of the instrument. The same or a second similar transfer means can be used to remove the sachet from the test position after the test is completed.

The invention also includes apparatus for testing the physical properties of a sequence of samples of material which is a combination of a) apparatus comprising dies which are moveable between a closed position in which a test on a sample can be carried out, and an open position in which samples can be loaded or removed, with b) means for arranging that before a test is carried out on a sample, the surfaces of the sample which would otherwise be in contact with the dies during a test can be covered by a film, and means for removing each sample from the test position after the dies have been reopened following the completion of a test. Preferably the apparatus also includes automatic mechanical means for conveying each of a series of samples individually and directly or indirectly from a location external to the dies to the test position between the dies.

In a preferred form of apparatus, means b) comprise means for intermittently drawing a strip of film through the space between two dies when the dies are in the open position, automatic mechanical means for loading each sample to be tested on to the strip, and means to dispense and means to direct film such that each sample on the strip can be covered with film before or during closure of the dies.

As indicated above, the invention has particular application to the operation of instruments for determining the viscoelastic properties of rubber and similar materials, which instruments comprise dies which are rotatable relative to one another. Tests with such instruments are usually carried out at temperatures above room temperature, for example at temperatures within the range 100°–300° C., such as temperatures in the range 150°–250° C. it is therefore necessary that the film used in the present invention should be heat resistant and substantially retain its integrity at the operating temperature.

Tests with such instruments generally involve the application of an oscillatory torque to one die and measurement of torque thereby induced in the other die. Some instruments are intended mainly to study the viscoelastic properties of rubber during vulcanisation. For such studies, the angle of oscillation of the first die is comparatively small, for example from $\pm 0.1°$ to $\pm 1°$. Other instruments, for example the rotorless viscometer described in European Patent Application 90870151.9 are designed so that the first die is capable of oscillating through larger angles, for example up to $\pm 90°$. In the method of the present invention, however, the film needs to be able to withstand the twisting distortion imposed by the relative rotation of the dies. It would be expected, therefore, that the choice of films meeting the necessary criteria would be wider when operating at low angles of oscillation, for example up to $\pm 5°$, than when operating at relatively large angles of oscillation.

Various polymer films have non-adhesive and thermal characteristics which make them suitable for use in the present invention as known, for example aromatic polyesters, polyamides and polyimides. Films of various thicknesses can be used. Apart from cost, however, a limitation in this respect is that the film should be pliable and extensible enough to conform accurately to the shape of the surfaces of the dies. For example, the dies in certain instruments are provided with alternating radial ribs and grooves to minimise slipping between the dies and the sample. Overall, however, the selection of a film which is acceptable under a particular set of test conditions and having the required balance of strength and thickness is essentially a matter of simple experimentation, but generally, film thickness in the range 10–50 $\mu$m would be expected to be suitable. Polyester film having a thickness in the range 15–30 $\mu$m, more especially in the range 20–25 $\mu$m, has been found to be particularly suitable, for example polyester film based on polyethylene terephthalate. Such films typically have a tensile strength at break in the range of 175–215 MPa in the machine direction and 225–275 MPa in the transverse direction, a yield stress in the range 85–105 MPa in both directions, and an elongation at break in the range 110–140% in the machine direction and 70–90% in the transverse direction. These values are determined by ASTM method D-882-83 carried out at 23° C., 50% relative humidity and a strain rate of 50%/min.

Certain polyamide, polyimide, mixed polyimide/polyamide and polyester ether ketone films can also be used, for example 'Kapton' polyimide film. In addition, metallised (metal coated) polymer films would be expected to be suitable as well as certain metallic films or foils. Tests using the method of the invention have shown that, at least with the preferred polyester films referred to above, the presence of the film lining to the die cavity does not, in most cases, significantly change the results compared with those obtainable in the absence of the film. In other instances, the presence of the film may cause a change in the results, but it is a constant change which gives comparative results.

Figure 2A:
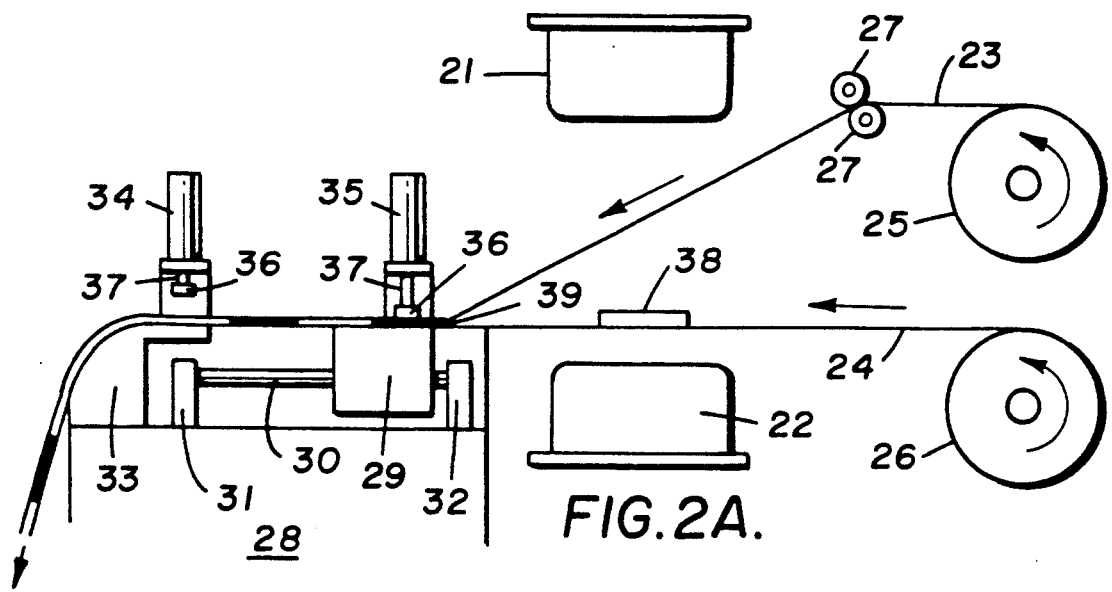
Figure 2B:
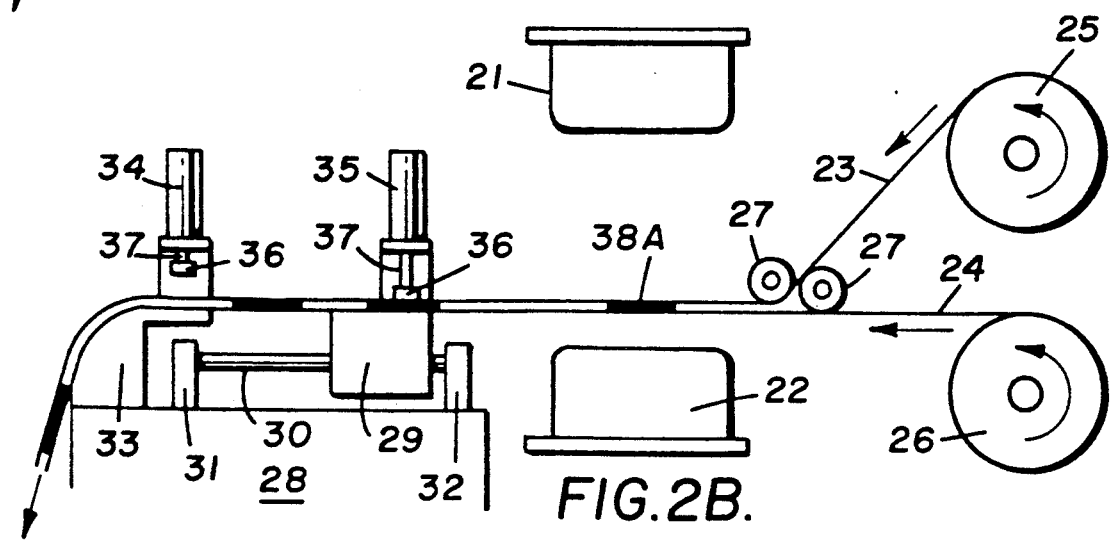

Embodiments of the invention are illustrated in FIGS. 1, 2A and 2B of the drawings which are schematic side views. FIG. 2A shows apparatus as one stage of its operations; FIG. 2B shows the same apparatus at a different stage of its operation.

In FIG. 1, upper and lower cylindrical die platens (1) and (2) which house upper and lower dies, are shown in the open position. Film (3) which acts as a support and conveyor for test samples is unwound from a roll (4) and passes first over a loading tray (5) located between the roll (4) and the lower die platen (2), then over the die in the lower die platen (2). A second band of film (6) is unwound from a roll (7) and is directed towards the first film by a guide roller (8). At the entry to the zone between the upper and lower dies, the second film lies between the upper die and the upper surface of the samples. The width of each film is slightly greater than the diameter of the platens. Both films pass between rollers (9) and (10) which act as a haul-off drive for the conveyor system. Three samples in positions (11), (12) and (13) are shown. Position (11) is the loading position where fresh samples are introduced on the film (3). Position (12) is the test position; the sample in position (12) is shown compressed as it appears at the end of a test, while the sample in position (13) has been removed from the test position, having been the subject of the previous test.

In operation, the haul-off drive is activated, with the die platens (1) and (2) in the open position, to convey the sample at position (11) to the test position (12) and concurrently to remove the sample from the test position (12). The die platens (1) and (2) are then closed and the required test is carried out on the sample. After the completion of the test, the die platens are opened. The haul-off drive is re-activated to remove the just-tested sample and to convey the next sample from position (11) to the test position (12), the sequence being repeated as often as necessary to complete tests on a series of samples.

In FIGS. 2A and 2B, upper and lower cylindrical die platens (21) and (22) which house upper and lower dies, are shown in the open position. The system employs two bands of film (23) and (24), each having a width slightly greater than the diameter of the platens, and which are drawn from rolls (25) and (26). Film (23) passes between guidance rollers (27) which are mounted to be pivotable between the position shown in FIG. 2A and the position shown in FIG. 2B.

The films (23) and (24) continue through the space between the platens (21) and (22), and finally through a haul-off device generally indicated as (28). The haul-off device comprises a block (29) which is slideable on parallel rods (30) (only one is shown) mounted in end supports (31) and (32), and a support plate (33), operating in conjunction with clamps (35) and (34) respectively. The clamps are essentially pneumatically operated cylinders, each having a foot (36) attached to the external end of a cylinder rod (37), so that each foot is moveable into and out of contact with the upper surface of the film (23). Clamp (35) is arranged to travel with the block (29), while clamp (34) is fixed relative to support plate (33).

FIG. 2A shows the beginning of a test cycle, with films (23) and (24) held apart in the space between platens (21) and (22) by guidance rollers (27) to allow a sample to be tested (38) to be placed on film (24) in the test position. A previously tested sample (39), sandwiched between the two films, is held between foot (36) of clamp (35) and block (29). Platens (21) and (22) are then brought together and the dies closed over sample (38), while concurrently, guidance rollers (27) are lowered to the position shown in FIG. 2B. When the test on the sample is complete, the platens (21) and (22) are reopened, and the just-tested sample (38A) remains sandwiched between films (23) and (24) as shown in FIG. 2B. By activation of pneumatic means (not shown), block (29) and clamp (35) are moved a preset distance in the direction of clamp (34), thereby unwinding more film from rolls (25) and (26) and removing the just-tested sample (38A) from the test position. Foot (36) of clamp (34) is then lowered to clamp the film between the foot and the support plate (33), while at the same time, foot (36) of clamp (35) is raised. Clamp (35) and block (29) are then returned to their first position, clamp (34) is released and clamp (35) is reapplied. Guidance rollers (27) are then raised to the position shown in FIG. 2A, and the sequence is repeated.

A particular merit of the use of film in accordance with the present invention is that it allows each sample to be given a machine-readable identification, for example a bar code, affixed to or printed on the film adjacent to the sample concerned. This identification can, for example, be used to set the operating parameters of the test instrument before the sample is conveyed into the test position.

We claim:

1. A method of operating an instrument for testing the physical properties of materials in which each of a series of samples of the material to be tested is placed in a test position located between dies, the dies are closed to mould the material to a test shape, a test is carried out on the sample in the mould and after the completion of the test the dies are opened and the sample is removed from the test position, characterised in that a film of material which is substantially non-adhesive to the dies under the conditions of the test covers those surfaces of the sample which, in the absence of the film, would be in contact with the dies during the test, each sample in turn is conveyed to the test position and removed by mechanical means from the test position after the completion of the test.

2. A method according to claim 1 in which each sample in turn is conveyed to the test position by automatic mechanical means.

3. A method according to claim 2 in which film is provided to cover those surfaces of the sample which, in the absence of the film would be in contact with the dies during the test and to extend beyond those surfaces, and the film which extends beyond the said surfaces of the sample is utilised in effecting at least the removal of the sample from the test position.

4. A method according to claim 2, in which the mechanical means for conveyance and removal comprise a strip of the said film which passes through the test position and is arranged to act as a conveyer belt, samples to be tested are located on the strip upstream of the test position, and are in turn conveyed to the test position and removed from the test position by intermittent activation of conveyer belt drive means, the samples having been covered by a said film before closure of the dies is complete.

5. A method according to either of claim 1 and 2 in which the mechanical means for removing the sample from the test position comprise a strip of said film which passes through the test position and is arranged to act as a conveyor belt, and, with the dies in the open position, each sample to be tested is in turn loaded onto the strip in the test position such that the strip forms a barrier between the sample and the surface of one die, film is interposed between the sample and the surface of a second die before closure of the dies is complete, and the film-enclosed sample is removed from the test position, after the completion of a test and reopening of the dies, by actuation of conveyor belt drive means which engage the strip.

6. A method according to claim 2 in which each sample is encased in an individual sachet of said film, and a mechanical means transfers the sachet from an external position to the test position, and a mechanical means removes the sachet from the test position after the completion of the test and reopening of the dies.

7. A method according to claim 6 in which said mechanical means comprise means for gripping the sachet where the film extends beyond the surfaces of the sample.

8. A method according to any of claim 1 to 4, 6 and 7 for testing the viscoelastic properties of rubber and like materials, in which the dies are heatable and relatively rotatable and the test comprises applying an oscillatory rotational motion to one die, and measuring the torque induced in the other die, the film of polymeric material being selected to be heat and tear-resistant under the conditions of the test.

9. A method according to claim 8 in which the film has a thickness in the range 10–50 $\mu$m and the test is carried out at a temperature not exceeding 300° C.

10. A method according to claim 9 in which the test is carried out at a temperature not exceeding 200° C. and the film is polyester or reinforced nylon film having a thickness in the range 15 to 30 $\mu$m.

11. A method according to any of claims 1 to 4, 6, 7, 9 and 10 in which each sample is provided with a machine-readable identification on the film adjacent to the sample.

12. Apparatus for testing the physical properties of a sequence of samples of material, which apparatus comprises dies which are movable between a closed position in which a test on a sample can be carried out, and an open position in which samples can be loaded or removed, characterised in that the apparatus also comprises a film and means for arranging that before a test is carried out on a sample, the surfaces of the sample which would otherwise be in contact with the dies can be covered with the film, and means for removing each sample from the test position after the dies have been reopened following the completion of a test.

13. Apparatus according to claim 12 which also comprises automatic mechanical means for conveying each of a series of samples individually and directly or indirectly from a location external to the dies to the test position between the dies.

14. Apparatus according to claim 13 having means for intermittently drawing a strip of film through the space between the dies when the dies are in the open position, automatic mechanical means for loading each sample to be tested on the strip, and means to dispense and means to direct film such that each sample on the strip can be covered with film before or during the closure of the dies.

* * * * *